United States Patent [19]

Handa et al.

[11] 4,346,712
[45] Aug. 31, 1982

[54] RELEASABLE BALLOON CATHETER

[75] Inventors: Hajime Handa; Yasuhiro Yonekawa; Sen Yamagata; Waro Taki, all of Kyoto; Yoshito Ikada; Hiroo Iwata, both of Uji, all of Japan

[73] Assignee: Kuraray Company, Ltd., Kurashiki, Japan

[21] Appl. No.: 121,036

[22] Filed: Feb. 13, 1980

[30] Foreign Application Priority Data

Apr. 6, 1979 [JP] Japan .................................. 54-42197
Sep. 14, 1979 [JP] Japan ................................ 54-118634

[51] Int. Cl.³ ............................................ A61B 17/12
[52] U.S. Cl. .................................. 128/325; 128/349 B
[58] Field of Search ............................... 128/349, 325

[56] References Cited

U.S. PATENT DOCUMENTS 3,911,927 10/1975 Rich et al. ...................... 128/349 R

FOREIGN PATENT DOCUMENTS 2613672 10/1977 Fed. Rep. of Germany ...... 128/325
2725755 2/1978 Fed. Rep. of Germany ...... 128/325
7712902 3/1978 France ................................. 128/325
7707490 10/1978 France ................................. 128/325
925756 1/1977 U.S.S.R. .............................. 128/325

OTHER PUBLICATIONS

Debrun (Neuroradiology 1975, 9: pp. 267-271), (J. Neurosurgery 1978, 49: pp. 635-649).
Serbinenko (J. Neurosurgery 1974, 41: pp. 125-145).
Pevsner, Micro Balloon Catheter, Am. J. Roentgenol, 128: pp. 225-230, 2/77.

Primary Examiner—Stephen C. Pellegrino
Assistant Examiner—Nancy A. B. Swisher
Attorney, Agent, or Firm—Oblon, Fisher, Spivak, McClelland & Maier

[57] ABSTRACT

This invention provides a releasable balloon catheter having a tube cuttable by torsion or a tube cuttable by heating at a joint part between the catheter body and the balloon. When the balloon catheter is inserted into a vessel and carried to the desired site by the blood stream and the balloon is inflated by introducing a fluid into the balloon and is fixed at the desired site face-to-face with the wall of the vessel, torsion or heating causes the balloon to be released from the catheter body. The balloon catheter is used to embolize vascular lesions.

12 Claims, 15 Drawing Figures

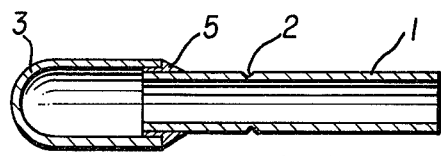
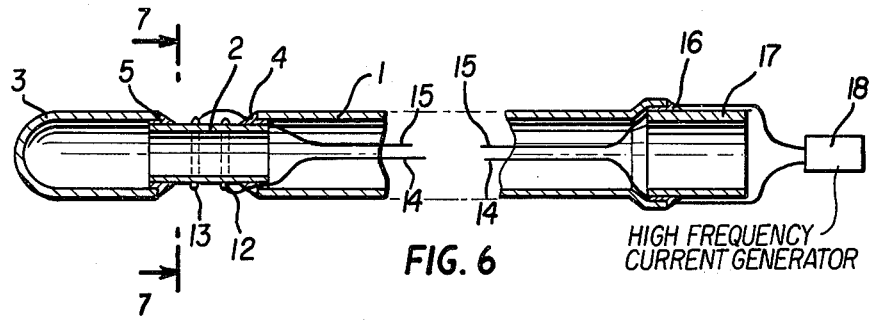
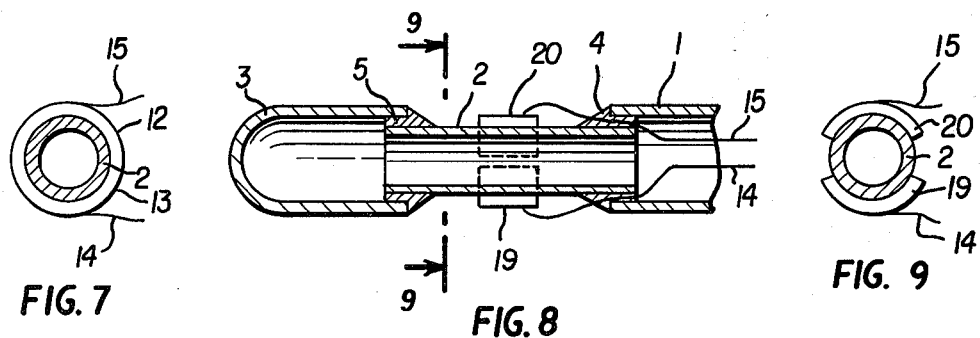
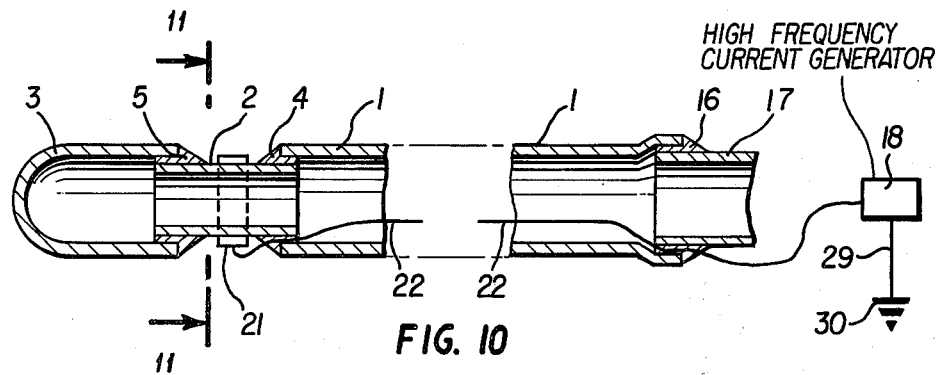
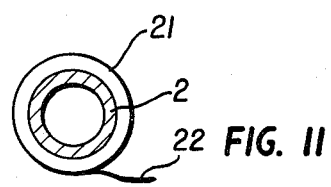

RELEASABLE BALLOON CATHETER

BACKGROUND OF THE INVENTION

1. Field of the Invention

This invention relates to a releasable balloon catheter, and more specifically, to a releasable balloon catheter for use in occluding or embolizing a vascular lesion.

2. Description of the Prior Art

Catheters have been used as essential medical instruments for diagnosis and treatment. In recent years, it has been made possible to insert a so-called balloon catheter having at its tip an inflatable and shrinkable balloon into the inside of a minute vessel along a blood stream, which cannot be reached by means of conventional catheters not provided with a balloon. This has further increased the range of application of catheters.

In an inflated balloon can be released from the tip of a catheter at the desired site, the treatment of various vascular lesions, which has been impossible by conventional techniques, will be able to be achieved. An example is the application of balloon catheters to the treatment of aneurysm, arteriovenous malformation and arteriovenous fistula which are typical vascular disorders. For example, by keeping an inflated balloon within an aneurysm, a serious sequela in the event of rupture of the aneurysm can be prevented. Or by occluding a vessel leading to a malformed arteriovein with a released balloon, a sequela of arteriovenous malformation incident to bleeding can be prevented. Furthermore, if an arteriovenous fistula can be occluded, the blood flow in an artery can be restored to one close to a normal condition.

As is clear from a few examples given herein, if a catheter having a releasable balloon is developed, it will be a great boon to patients suffering from cerebrovascular disorders and cardiovascular disorders which occupy the first and third places, respectively, of mortality in Japan. The great significance of the development of such a catheter is clear in view of the fact that this new method of treatment does not require any surgical operation, but can be achieved simply by injection.

The site at which the balloon is desired to be released is mainly a vascular lesion which is located deep inside the body. Accordingly, it is required that the balloon should not be released from the main portion of the catheter until it reaches this site, and that the balloon should be released even at such a site which is deep inside the body.

Prior to the present invention, two types of catheter with a releasable balloon have been devised for vascular occlusion. In one type, first reported by Debrun (Neuroradiology 1975, 9:267~271 and J. Neurosurgery 1978, 49:635~649), the balloon is firmly tied to a Teflon catheter with elastic threads and is released with the help of a second coaxial polyethylene catheter. The disadvantage of this type is that the catheter is difficult to introduce beyond many arterial curves such as the carotid siphon, because of its lack of flexibility. Its use also requires a relatively large coaxial catheter. The other has been reported by Serbinenko (U. Neurosurgery 1974, 41:125~145), who attaches a balloon to a polyethylene catheter which grips the catheter due to its elasticity. The balloon is released simply by pulling on the catheter. This type of catheter can be used with lesions on many branches of the arterial tree. It has the danger that it can be released accidentally. It can also damage the vascular lesion if it is pulled on.

An attempt was made to remedy these defects. Japanese Laid-Open Patent Publication No. 132580/1977 discloses a balloon catheter in which the balloon is fixed to the main portion of the catheter by securing a C-type spring to a joint part between them. In such a balloon catheter, the C-type spring is released when the pressure in the balloon exceeds a specified limit by the pressure of a fluid introduced into the balloon. Thus, the balloon is released from the catheter. However, the balloon catheter of this type has the disadvantage that there are some cases where the balloon is released in a place other than the desired site and cannot be released when desired, because it is difficult to adjust the pressure applied by the C-type spring.

SUMMARY OF THE INVENTION

It is therefore an object of this invention to provide a releasable balloon catheter which can be easily inserted into vessels and which can be released at the desired site with certainty.

Another object of this invention is to provide a releasable balloon catheter which can be inserted into minute vessels and does not injure the walls of the vessels.

Still another object of this invention is to provide a releasable balloon catheter which can be easily produced.

These objects can be achieved by a releasable balloon catheter including (i) a tubular catheter body, (ii) an inflatable balloon provided at one end of the catheter body so that a fluid is introduced into the balloon from the catheter, and (iii) (a) a tube cuttable by torsion or (b) a tube cuttable by heating, the tube (a) or (b) being provided at or near a joint part between the balloon and the catheter body, the balloon catheter being constructed such that when the balloon catheter is inserted into a vessel and carried to the desired site by the blood stream and the balloon is inflated by the introduction of a fluid into the balloon through the catheter body and is fixed face-to-face with the wall of the vessel at the desired site, a torsional force is applied to the tube (a) cuttable by a torsion or heat is applied to the tube (b) cuttable by heating, thereby to effect cutting at the cuttable tube (a) or (b) and thus to release the balloon from the catheter body.

BRIEF DESCRIPTION OF THE DRAWINGS

Other objects of this invention will become apparent from the following description.

FIG. 5 is a longitudinal sectional view showing another embodiment of the balloon catheter of this invention which contains a notched portion 2 as the portion cuttable by torsion at the end of a catheter body 1;

FIG. 6 is a longitudinal sectional view showing yet another example of the balloon catheter of this invention, which has provided therein a tubular member 2 as the portion cuttable by heating, which is adapted to be heated by electrodes 12 and 13 composed of conductor wires;

FIG. 7 is a cross-sectional view taken along the line 7—7 of FIG. 6;

FIG. 8 is a longitudinal sectional view showing another example of the balloon catheter of this invention, which has provided therein a tubular member 2 as the portion cuttable by heating, which is adapted to be heated by electrodes 19 and 20 composed of conductive metallic foil;

FIG. 9 is a cross-sectional view taken along the line 9—9 of FIG. 8;

FIG. 10 is a longitudinal sectional view showing another example of the balloon catheter of this invention, which has provided therein a tubular member 2 as the portion cuttable by heating, which member is adapted to be heated by a monopolar electrode 21;

FIG. 11 is a cross-sectional view taken along the line 11—11 of FIG. 10;

DETAILED DESCRIPTION OF THE PREFERRED EMBODIMENTS

Figure 1:
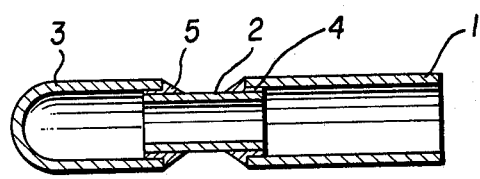
FIG. 1 is a longitudinal sectional view showing one example of the balloon catheter of this invention which contains a tubular member 2 as a portion cuttable by torsion.

Referring to FIG. 1, the balloon catheter of this invention includes (i) a tubular catheter body 1, (ii) an inflatable balloon 3 provided at one end of the catheter body so that a fluid is introduced into the balloon from the catheter, and (iii) a portion 2 cuttable by torsion provided at a joint part between the balloon and the catheter body. The other end of the catheter is not shown in the drawings. Usually, the catheter 1 extends a predetermined length (the length being selected as desired depending upon the desired use) to form the other end into which an injecting syringe is usually inserted for introduction of a fluid into the catheter by an injector. The portion 2 cuttable by torsion is made of a tube having a weaker torsion strength than the catheter body 1. When the other end of the catheter body which is not inserted into a vessel is twisted, cutting occurs at this tube 2. The tube 2, the catheter body 1 and the balloon 3 are connected to each other by an adhesive (e.g. cyanoacrylate or epoxy type adhesives). Resin layers 4 and 5 are formed so that the catheter body, tube and balloon are connected to each other continuously to form a smooth surface. If the joint part between the tubular member 2 and the catheter body 1 is smoothed by means of an adhesive 4, the balloon catheter will not injure vessels at the time of catheterization.

Figure 2:
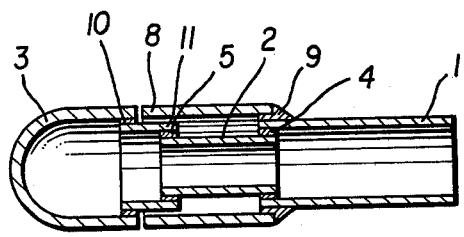
FIG. 2 is a longitudinal sectional view showing another example of the balloon catheter of this invention which further has a cover 8 for preventing the flexural breaking of the tubular member 2 at the time of insertion into a vessel.

FIG. 2 shows another embodiment of the balloon catheter of this invention. This embodiment is preferred when the tubular member 2 has a low flexibility and is likely to be broken upon bending at the time of catheterization. A cover 8 is provided at the terminal portion of the catheter body 1 so as to cover the member 2. The cover 8 is cemented by means of an adhesive 9. Preferably, the cover 8 is made of a tubular material having resistance to breakage upon bending (for example, silicone rubber). A sheet 11 which is made of polyethylene tube, etc., is provided to prevent bending breakage of the balloon 3 and further to facilitate catherization. The sheet 11 is fixed to the balloon 3 and the member 2 by adhesives 5 and 10. In FIG. 2, as a result of providing the cover 8 and the sheet 11, there is some gap between the tip of the cover 8 and the end of the balloon 3. Hence, the member 2 is prevented from bending and breaking. Furthermore, since the top surface of the cover 8 and the top surface of the balloon 3 are smooth, the catheter can be easily inserted into a vessel and does not injure the vascular walls.

Figure 3:
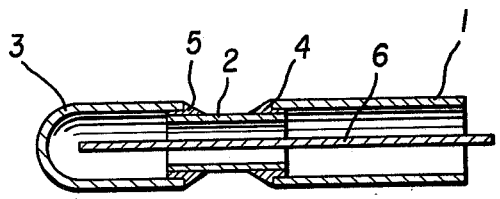
FIG. 3 is a longitudinal sectional view of still another example of the balloon catheter of this invention which has a rigid core material 6 inserted into the cavity of the tubular member 2 cuttable by torsion to prevent the flexural breaking of the member 2 at the time of insertion into a vessel.

Still another embodiment in which the member 2 has low flexibility and is likely to be broken upon bending is shown in FIG. 3. In this embodiment, a rigid core material 6 (e.g., a nylon fishing gut or a resin-dipped polyester thread is inserted into the cavity of the member 2 to prevent the flexural breaking of the member 2. When this balloon catheter is inserted into a vessel and the balloon is to be released within the vessel, the core material 6 is pulled out immediately before the releasing of the balloon.

When the member 2 is likely to be broken upon bending at the time of inserting an intravenous catheter, it is also possible to coat the periphery of the member 2 with a hydrophilic polymer, especially a water-soluble polymer such as polyvinyl alcohol, starch or dextran. The water-soluble polymer to be coated at this time should be non-toxic even when it dissolves in the blood.

Figure 4:
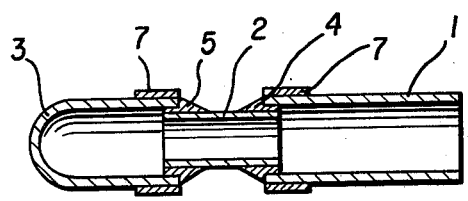
FIG. 4 is a longitudinal sectional view of a further example of the balloon catheter of this invention which has X-ray impervious metallic pieces 7 secured thereto so that the cutting of the tubular member 2 cuttable by torsion within a vessel can be ascertained.

Referring to FIG. 4, an X-ray impervious metallic piece 7 is fixed to both sides of a tubular member 2, i.e. to the terminal portions of the balloon and the catheter body. The piece is made of a material such as stainless steel, titanium or cobalt-chromium alloy. This construction enables the distance between the two metallic pieces to be known by radiography. It is possible therefore to ascertain that the tubular member is twisted off within a vessel to release the balloon.

Still another embodiment of this invention is shown in FIG. 5. In this embodiment, a notched portion 2 is provided at the periphery of the terminal portion of the catheter body 1 as a portion which can be cut by torsion. Preferably, the portion is provided within 10 mm (more preferably 1 mm) from the terminal portion of the catheter body.

The balloon catheter shown in FIG. 5 has the disadvantage that the member 2 is liable to be broken at the notched portion when inserted into the blood vessel. Further, the member 2 is more difficult to produce than that shown in FIG. 1. Therefore, this embodiment is not preferred.

The individual portions of the above embodiments, i.e., the balloon catheters having a portion cuttable by torsion, are described in detail below.

One characteristic feature of this invention is that a portion which is cuttable by torsion is provided in a balloon catheter. When this portion is to be composed of a tubular material, it must have a lower torsional strength than the catheter body. The torsion strength of the member 2 is determined according to the site of a vessel used. The member 2 is in the form of a tube or hollow fiber, and its thickness, outside diameter and length cannot be determined according to a single parameter because they depend upon the size and shape of a vessel to be occluded. Usually, the member 2 has a wall thickness of 10 to 400 microns, preferably 10 to 200 microns, an outside diameter of 100 to 1000 microns, preferably 200 to 700 microns, and a length (the length from the end of the balloon 3 to the end of the catheter body 1) of 2 to 20 mm, preferably 2 mm to 15 mm.

The material for the member 2 may be any material which meets the above physical conditions. Examples include polyethylene, polypropylene, polyvinyl alcohol, vinyl alcohol copolymers (such as an ethylene-vinyl alcohol copolymer with an ethylene content of 10 to 60 mole%), nylon, polyethylene terephthalate, regenerated cellulose, and cellulose derivatives. Polyvinyl alcohol, vinyl alcohol copolymers and regenerated cellulose are preferred. The above polyvinyl alcohol includes acetalized polyvinyl alcohol obtained by acetalization with formaldehyde, glutaraldehyde, etc. to a degree of acetalization of 1 to 50 mole%.

The outside diameter and the wall thickness of the catheter body 1 are determined according to a vessel into which it is inserted, and are within the same ranges as those described above for the member 2. Usually, the catheter body has a slightly larger outside diameter than the member 2. It is necessary that the catheter body 1 should have a higher torsion strength than the member 2. It should have a tensile strength such that it does not break upon catheterization. Preferably, the catheter body 1 is a thin tube, for example, a hollow fiber, having a Young's modulus in the wet state (in water at 25° C.) of 1 to 100 kg, preferably 2 to 20 kg, so as to permit easy insertion into minute, bent vessels. The Young's modulus is measured by using an ordinary tensile tester at a tensile speed of 10 cm/min. in water at 25° C. using a sample having a length of 5 cm. The material for the catheter body 1 may be the same as those described above for the member 2. Preferably, it is made of polyethylene or teflon which is used in ordinary catheter bodies.

The balloon 3 used in this invention may be made of a material which has required elasticity and can endure sterilization. Rubbers (natural, synthetic and silicone rubbers) are preferred. The shape and size of the balloon 3 are determined depending upon the type of a vessel. Usually, it is in the form of a cylindrical cap shown in the drawings. To permit easy insertion into bent minute vessels, the balloon in the non-inflated state should have as small a thickness as possible, for example less than 500 microns, preferably less than 200 microns.

Now, a balloon catheter having a portion which is cuttable by heating is described in detail. FIG. 6 shows one example of this type. The balloon catheter has a portion 2 cuttable by heating between a catheter body 1 and a balloon 3. This portion 2 is a tubular member composed of a material which is melted or dissolved in blood when heated. Bipolar electrodes 12 and 13 composed of conductor wires are secured to the portion 2 so as to heat the tube whenever necessary.

The tubular member 2 which is melted by heating is a solid at the body temperature. A suitable material for it is one which does not easily break by an external force, is easily melted or dissolved within a vessel at a temperature above the body temperature but below the temperature at which water is vaporized (100° C.), and which is not toxic to the living body even when melted or dissolved in the blood. Preferably, the material should be easily processable, and be flexible. An example of such a material for the member 2 is a hydrophilic polymer. Above all, polyvinyl alcohol and vinyl alcohol copolymers (e.g., an ethylene/vinyl alcohol copolymer having an ethylene content of 10 to 60 mole%) are suitable. The shape of the member 2 is a tube or hollow fiber as described hereinabove. Its outside diameter, thickness and length cannot be determined according to a single parameter because they depend upon the size and shape of a vessel to be occluded. Usually, it has an outside diameter of 100 to 1000 microns, preferably 200 to 700 microns, a wall thickness of 10 to 400 microns, preferably 10 to 200 microns, and a length (the length from the end of the balloon 3 to the end of the catheter body 1) of 2 to 50 mm, preferably 5 to 30 mm.

The bipolar electrodes 12 and 13 may be provided not only exteriorly of the member 2 as shown in FIG. 6, but also interiorly of the member 2 or may be embedded in the member 2. These electrodes 12 and 13 are connected to a high frequency current generator 18 through lead wires 14 and 15. The member 2 is melted as a result of the high frequency current passing across the electrodes 12 and 13. Preferably, the distance between the electrodes 12 and 13 is as short as possible because the member 2 can be melted or dissolved more exactly within a shorter period of time. The lead wires 14 and 15 are electrically conductive, and are made of a material which is free from leakage, allows only a minimum of heat generation, is flexible, and which can be very intricately processed. For example, enamelled copper wires are preferred. The lead wires 14 and 15 lead to the high frequency current generator 18 along the outside of a tube 17 provided at the other end of the balloon catheter through a bonded part 16 between the tube 17 and the catheter body 1.

When a very flexible catheter body is used, a heating mechanism utilizing a high frequency current as shown in FIG. 6 is preferred. When the catheter body is slightly hard and has such a flexibility of fiber as to permit transmission of laser, the heating mechanism may be the one based on laser.

The member 2, balloon 3 and catheter body 1 are bonded to each other by means of an adhesive (e.g., cyanoacrylate or epoxy type adhesives). In this case, as in the balloon catheter shown in FIG. 1, adhesive layers 4 and 5 are formed so that the bonded portions between the member 2 and the balloon 3 and the catheter body 1 form a smooth surface (see FIG. 6). The balloon used in this invention is the same as that described hereinabove. The catheter body used in this embodiment may be the same as that described hereinabove. It may also be made of a silicone polymer, polyurethane, thermoplastic polyesters (e.g., polybutylene terephthalate), a silicone-polyurethane copolymer, soft vinyl chloride resin, and an ethylene/vinyl acetate copolymer. Of these, silicones are preferred. When the tubular member is to be cut off by torsion, the torsion strength of the catheter body needs to be higher than that of the tubular member. Thus, the catheter body is required to have a certain hardness. Accordingly, the catheter body in this case should desirably have a Young's modulus within the above-specified range. However, in the case of the balloon catheter shown in FIG. 6, such properties are not required, and a flexible material may be used.

In FIG. 8, electrodes 19 and 20 composed of conductive metal foil are placed on the top and bottom of the member 2 as heating mechanisms, and each end of the metal foils is secured to the member 2 by an adhesive 4.

In FIG. 10, a monopolar electrode 21 composed of a bare conductive wire is wrapped around the member 2 as a heating mechanism. A conductor wire 22 is connected to a high frequency current generator 18, and another conductor wire 29 leads from an opposite electrode on the body surface 30 of a patient to the high frequency current generator 18. Generally, the electrode which is made of a metal plate (50×30 cm) is set on the back, the belly or the thigh of the patient.

Figure 12:
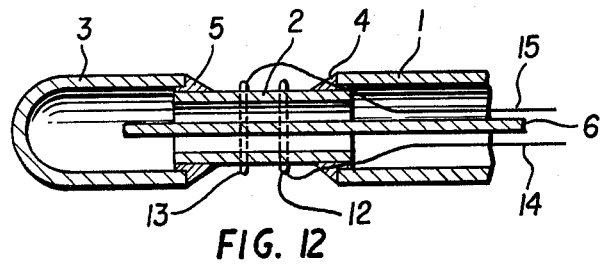
FIG. 12 is a longitudinal sectional view showing another example of the balloon catheter of this invention, which includes a tubular member 2 cuttable by heating, conductor wire electrodes 12 and 13 and a rigid core material 6 for preventing the flexural breaking of the member 2 at the time of insertion into a vessel.
Figure 13:
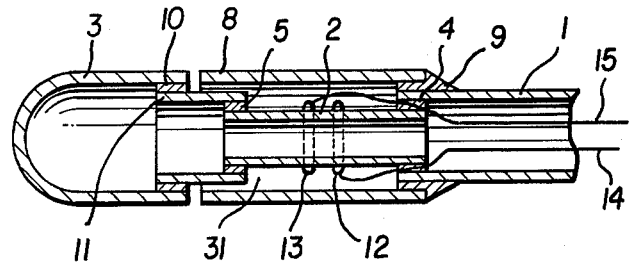
FIG. 13 is a longitudinal sectional view showing another example of the balloon catheter of this invention, which includes a tubular member 2 cuttable by heating, conductor wire electrodes 12 and 13, and a cover 8 for preventing the flexural breaking of the member 2 at the time of insertion into a vessel.
Figure 14:
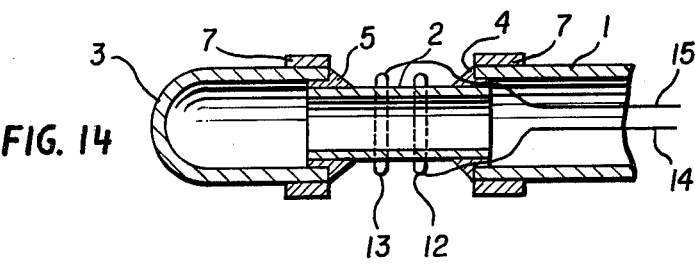
FIG. 14 is a longitudinal sectional view of another example of the balloon catheter of this invention, which includes a tubular member 2 cuttable by heating, conductor wire electrodes 12 and 13, and X-ray impervious metallic pieces 7 for ascertaining the cutting of the member 2 within the vessel.

When the member 2 is likely to be broken upon bending in catheterization, it is possible to insert a core material into the inner cavity of the member 2 (FIG. 12), or to provide a cover so as to cover the tubular member (FIG. 13). The space 31 shown in FIG. 13 may be filled with a viscous aqueous solution containing water soluble polymer, for the purpose of preventing the thrombus which is likely to be formed at the time of contact of blood with the heated portions. The embodiment shown in FIG. 14 is used when it is necessary to ascertain that the tubular member is cut off by heating and the balloon is released.

Among the various embodiments described above, the embodiments shown in FIGS. 6 and 13 are frequently used. When a balloon catheter having a portion cuttable by torsion is compared with that having a portion cuttable by heating, it is noted that the former (torsion-type) requires a certain degree of hardness at its body portion, and therefore, as far as cerebral vessels are concerned, it is useful for occluding the supracallosal portion of the anterior cerebral artery and M3 portion of the middle cerebral artery, but is difficult to use for occlusion of more distal vessels. A torsional force can be transmitted well when the catheter is short. But when the catheter is long, for example when a vascular lesion of the basilar artery is to be occluded via the femoral artery, the torsional force is difficult to transmit. Thus, to transmit the torsional force well, a considerable length of the catheter from that end at which the torsional force is to be applied should be made of a hard material. Accordingly, the balloon catheter having a portion cuttable by heating is better.

The releasable balloon catheter of this invention is used in the following manner. The balloon catheter is introduced into a vessel, and by carrying the inflated balloon along a blood stream, the balloon catheter is conveyed to the desired vascular site. Then, through the catheter body, a curable liquid, etc. is introduced into the balloon to inflate the balloon further so that the balloon adheres closely, and is fixed, to the vascular wall at the desired site. Then, by applying a torsional force or heating, the cuttable portion of the tubular member is cut off to release the balloon. When it is necessary to ascertain the releasing of the balloon at this time, balloon catheters of the types shown in FIGS. 4 and 14 are used.

Since the releasable balloon catheter of this invention is of very simple structure as described above, it is easy to produce at a low cost. It is also safe because the balloon is never released from the catheter body unless a torsional force is applied to the catheter or the severable tube is heated to a temperature above the body temperature. Furthermore, because the severable tube is cut off accurately, the balloon does not deviate from the desired site, and is released without injuring the vascular wall. Accordingly, the balloon catheter of this invention is very useful.

The following Examples illustrate the present invention more specifically. The invention, however, is not limited in any way by these examples.

EXAMPLE 1

As a member 2, a slender tube (outside diameter 250 microns, thickness 20 microns) made of cellulose was inserted into a vulcanized natural rubber balloon (outside diameter 400 microns, thickness 100 microns in the shrunken state) as shown in FIG. 1, and they were fixed to each other by a cyanoacrylate type adhesive 5. The cellulose tube was cut at a position 1 cm from the end of the balloon. A 1 mm portion of the other end of the cellulose tube was inserted into a chromic acid-treated catheter body 1 (made of polyethylene and having an outside diameter of 600 microns, a wall thickness of 180 microns and a length of 60 cm), and this portion was bonded by using a cyanoacrylate-type adhesive. The cellulose tube used had a tensile strength of 56 g and a torsion strength of 29 g. The polyethylene catheter had a tensile strength of 645 g, a Young's modulus of 3.8 kg, and a torsion strength of 108 g. These were measured in the wet state at 21° C. The torsion strength was measured by a tensile tester (Instron TMM) at a speed of 100 times/min. while adjusting the length of a sample to 5 cm.

After confirming that the bonding between the balloon and the cellulose tube and the bonding between the cellulose tube and the polyethylene catheter were sufficient, and the resulting balloon catheter had sufficient strength to repeated inflation and shrinkage by injecting water into the catheter from the other end of the polyethylene catheter using an injector, the balloon catheter was inserted into a long silicone tube having an inside diameter of 5 cm. Then, the balloon was inflated by water to bring the balloon wall into intimate contact with the inside wall of the silicone tube. When the end of the catheter was rotated by fingers, the cellulose tube was twisted off after six cycles of rotation, namely after giving six torsions to the catheter, and the balloon was released. Within about several minutes, the water inside the balloon flowed out, and the balloon shrank.

The above balloon catheter was inflated with a curable vinyl monomer liquid instead of water, and after the filled liquid cured, 7 cycles of rotation were given to the catheter. The balloon was thus released from the tip of the catheter, and remained inflated even after one day.

EXAMPLE 2

As a member 2, a slender tube (outside diameter 350 microns, wall thickness 35 microns) made of an ethylene/vinyl alcohol copolymer (ethylene content 33 mole%, to be referred to as EVA) having a tensile strength of 42 g and a torsion strength of 10 g was cemented to a vulcanized natural rubber balloon 3 (outside diameter 800 microns, wall thickness 100 microns in the shrunken state) through a sheet 11 composed of a polyvinyl alcohol tube by cyanoacrylate-type adhesives 5 and 10, as shown in FIG. 2. The EVA tube 2 was cut at a position 5 mm from the end of the balloon. Separately, a silicone tube cover 8 was fixed to the periphery of the same mixed chromic acid-treated catheter body 1 (polyethylene catheter having an outside diameter of 600 microns, a wall thickness of 180 microns and a length of 60 cm) as used in Example 1 by means of a cyanoacrylate-type adhesive 9. A 1 mm portion of the end of the EVA tube 2 produced as above was inserted into the polyethylene catheter, and the EVA tube 2 and the polyethylene catheter 1 were conded by means of a cyanoacrylate-type adhesive. After bonding, an epoxy-type adhesive was coated on a bonded peripheral portion 9 to make it smooth, and then allowed to solidify. The EVA tube fully adhered both to the balloon and the polyethylene catheter, and when the balloon was repeatedly inflated and shrunken by flowing water therethrough, the balloon catheter had sufficient strength.

When the releasable balloon catheter thus obtained was inserted into a silicone tube and subjected to a torsion test, the balloon was cut off from the catheter body after ten cycles of torsion. Because of the self-fusing property of EVA, the balloon remained inflated even after a lapse of 2 hours.

EXAMPLE 3

An adult dog was anesthetized with Nembutal, and then its left external carotid artery was punctured with an 18-gauge, 13 cm intravenous catheter. The inside portion was pulled out, and the outside Teflon catheter was inserted into a vessel. Through the Teflon catheter, the same releasable balloon catheter as produced in Example 2 was inserted into the vessel. The balloon catheter was conducted to the branch of the external carotid artery while inflating the balloon under X-ray fluoroscopy. After conducting the balloon to a site of occlusion, it was shrunken and the angiografin (contrast medium) in it was fully removed. A mixed liquid obtained by mixing a silicone primer and tetraethyl ortho-silicate in a ratio of 1:1 and adding a moderate amount of tin octylate was injected into the balloon. After the silicone was cured, the catheter was rotated. Thus, the EVA portion was twisted off, and the balloon was released from the catheter. The balloon stayed at the site of occlusion, and fully acted as an embolizing means.

EXAMPLE 4

The left neck of a patient with intracranial arteriovenous malformation at the corpus callosum was locally anesthetized with dibucaine, and the common carotid artery was punctured with an 18-gauge, 13 cm intravenous catheter. The outer Teflon sheath was inserted in the direction of the internal carotid artery under X-ray fluoroscopy. The same releasable balloon catheter as produced in Example 2 was inserted through the Teflon sheath. The balloon was inflated with a contrast medium, and led to the branch of the anterior cerebral artery along a blood stream. The anterior cerebral artery was a feeding artery of the intracranial arterivenous malformation of this patient. By embolizing it, the intracranial arteriovenous malformation could be treated. The balloon thus guided was temporarily shrunken, and the angiografin (contrast medium) in it was fully removed. Then, a mixed liquid obtained by mixing a silicone primer and tetraethyl ortho-silicate in a ratio of 1:1 and adding tin octylate was injected into the balloon. After the balloon occluded the branch of the anterior cerebral artery and the silicone was cured, the catheter was rotated to release the balloon from the catheter. No complication owing to this operation was noted.

EXAMPLE 5

As shown in FIG. 6, a natural rubber balloon 3 (outside diameter 800 microns, wall thickness 100 microns in the shrunken state) was secured to a polyvinyl alcohol tube 2 (outside diameter 500 microns, wall thickness of 100 microns), and they were bonded to each other by a cyanoacrylate-type adhesive. The bonded portion was coated with an epoxy resin to form a smooth surface. Two enamelled wires 14 and 15 (0.05 mm in diameter) were inserted through a silicone tube 1 (outside diameter 600 microns). From one end of the silicone tube, the enamelled wires were pulled outwardly, and the polyvinyl alcohol tube 2 was inserted into the silicone tube 1. They were bonded by a cyanoacrylate-type adhesive. The bonded portion was coated with an epoxy resin 4 to form a smooth surface. One of the enamelled wires pulled outwardly was brought to the end portion of the polyvinyl alcohol tube and loosely wrapped around it in a loop form after removing a part of the enamel, thereby forming an electrode 12. An electrode 13 produced by removing part of the enamel of the other enamelled wire was similarly wrapped around the central portion of the polyvinyl alcohol tube. The distance between the electrodes 12 and 13 was made as short as possible and adjusted to about 1.3 mm. On the other hand, the two enamelled wires extending from the other end of the silicone tube 1 were pulled out of the silicone tube, and a chrome-treated polyethylene tube 17 (outside diameter 600 microns, wall thickness 180 microns) was fitted into one end of the silicone tube and they were bonded by a cyanoacrylate-type adhesive. The bonded portion was coated with an epoxy resin 16 to form a smooth surface. After confirming that the sealing of the lead wire pulling portion was complete, short-circuiting between the electrodes 12 and 13 and between the lead wires 14 and 15 and the breaking of the lead wires were examined by testers. The balloon catheter was dipped in physiological saline, and then the enamel coating of the lead wires extending outwardly of the polyethylene tubing was removed, and the lead wires were connected to a high frequency current generating device 18 (a product of Aesclup Company). A curable liquid comprising 2-hydroxyethyl methacrylate and a polymerization initiator was injected into the balloon, and cured. Then, the output (Dosis) of the high frequency current generator was set at 3, and power was supplied. In about 1 second, the bonded portion 2 composed of the polyvinyl alcohol tube was dissolved, and the balloon 3 was separated from the catheter body 1 made of silicone tube.

EXAMPLE 6

Figure 15:
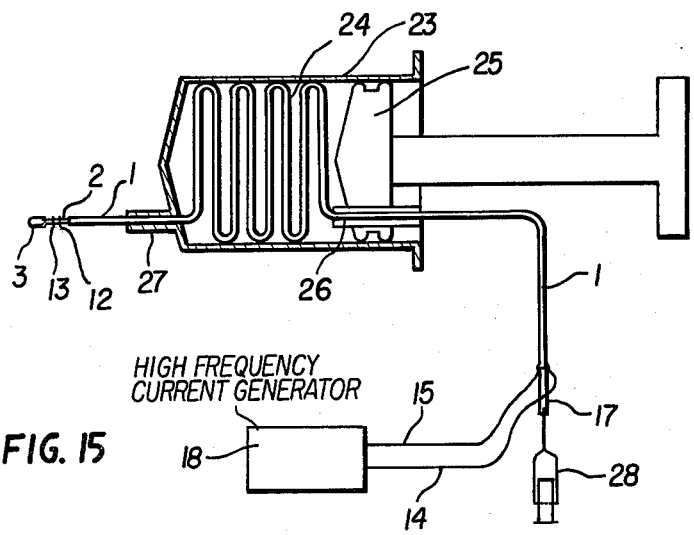
FIG. 15 is a longitudinal sectional view showing one example of an injector for inserting the balloon catheter of this invention into a vessel.

An adult dog was anesthetized, and an arteriovenous fistula was artificially made by the anastomosis of the external jugular vein and the common carotid artery. A sheath introducer having an Fr (French unit) of 5.5 was inserted into that portion of the carotid artery which was more on the heart side than the fistula. A balloon catheter produced in the same way as in Example 5 was inserted through the introducer. On the other hand, the lead wires and electrodes in the balloon catheter were well examined by testers to confirm that there was no short-circuiting between them. Since a silicone catheter was very flexible and could not be injected in opposition to the back flow of the blood from the sheath, it was injected as included in an injector 23 as shown in FIG. 15. Specifically, the balloon catheter was included in the injector 23, and injected into a vessel together with physiological saline 24 in the injector 23. In FIG. 15, the reference numeral 25 represents the tip of a rubber plunger, and 27, the outlet of the injector. The reference numeral 26 represents a metallic tube extending through the plunger tip 25. The silicone tube was passed through the metallic tube 26, and the space between them was sealed up with a resin. The reference numeral 28 represents a 1 cc syringe for introduction of a contrast medium, etc.

Then, the balloon was inflated with a contrast medium (metrizamide), and conducted to fistula portion. After the contrast medium was removed as much as possible, a photographable curable liquid comprising 2-hydroxyethyl methacrylate and a polymerization initiator was injected into the balloon to inflate it and thereby to embolize the fistula portion. After the liquid was cured, the lead wires were connected to a high frequency current generator (a product of Aesclup Company). When power was supplied for 1 second at an output (Dosis) of 3, the balloon was released from the catheter body. It was ascertained that only the fistula portion was occluded, and the four streams of the carotid artery were preserved.

The dog used in the experiment awoke well from anesthesia, and no adverse effect owing to this operation was seen to be exerted on the experimental animal.

EXAMPLE 7

An adult dog was anesthetized, and an arterial fistula was artificially made at the common carotid artery using a graft segment of the external jugular vein. In the same way as in Example 6, the same balloon as used in Example 5 was conducted to the arterial fistula. The same curable liquid as in Example 2 was injected into the balloon. After the liquid was cured, power was supplied at an output (Dosis) of 3 for 1 second to release the balloon. It was ascertained that the balloon occluded only the arterial fistula, and there was no constriction in the carotid artery. No adverse effect was seen to be exerted on the experimental animal.

EXAMPLE 8

An arteriovenous fistula was made artificially by anastomosing the common carotid artery and the external jugular vein in an adult dog. A polyethylene catheter having an Fr of 6.0 was inserted through the right femoral artery, and guided to the right carotid artery by the Seldinger's method. The same balloon catheter as produced in Example 5 was included in an injector in the same way as in Examples 6 and 7, and inserted into the carotid artery by the injector shown in FIG. 15 through the above catheter. The balloon was similarly guided to the fistula portion. Then, the same curable liquid as in Example 6 was injected to occlude the fistula portion by the balloon. Power was supplied for 1 second at an output (Dosis) of 3 using a high frequency current generator to release the balloon. No adverse effect was exerted on the dog.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A releasable balloon catheter, comprising:
a tubular catheter body;
an inflatable balloon provided at one end of said catheter body for holding a curable liquid introduced into the balloon from the catheter;
a severable tube formed at a joint part between said balloon and said catheter body and which comprises a hydrophilic polymer;
a plurality of bipolar electrodes secured to the severable tube through which a high frequency current is flowable;
means for generating a high-frequency current and connected to each of said bipolar electrodes; and
said balloon catheter being constructed such that when said balloon catheter is inserted into a vessel and carried to the desired site by the blood stream and the balloon is inflated by the introduction of said curable liquid into the balloon through the catheter body and is fixed face-to-face with the wall of the vessel at the desired site and said generating means communicates said high frequency current across said electrodes, said severable tube is heated so as to be melted or dissolved, such that said tube is cut to release said balloon from said catheter.

2. The releasable balloon catheter of claim 1, wherein said severable tube further comprises a tube having an outside diameter of 100 to 1000 microns, a wall thickness of 10 to 400 microns and a length of 2 to 50 mm.

3. The releasable balloon catheter of claim 1, wherein said catheter body further comprises a silicone resin tube and said severable tube further comprises a polyvinyl alcohol tube.

4. The releasable balloon catheter of claim 1, further comprising a cylindrical cover covering said severable tube so that said tube is prevented from flexural breaking upon catheterization.

5. The releasable balloon catheter of claim 1, further comprising a rigid core material in the inner cavity of said balloon catheter so that the severable tube is prevented from flexural breaking upon catheterization.

6. The releasable balloon catheter of claim 1, further comprising an X-ray impervious metal piece secured to the end portion of said catheter body and to said balloon so as to ascertain the releasing of the balloon from the catheter body by X-ray fluoroscopy.

7. A releasable balloon catheter, comprising:
a tubular catheter body;
an inflatable balloon provided at one end of said catheter body for holding a curable liquid introduced into the balloon from the catheter;
a severable tube formed at a joint part between said balloon and said catheter body and which comprises a hydrophilic polymer;
a monopolar electrode secured to the severable tube, through which a high frequency current is flowable;
means for generating a high frequency current and connected to said monopolar electrode; and
said balloon catheter being constructed such that when said balloon catheter is inserted into a vessel and carried to the desired site by the blood stream and the balloon is inflated by the introduction of said curable liquid into the balloon through the catheter body and is fixed face-to-face with the wall of the vessel at the desired site and said generating means communicates said high frequency current between said monopolar electrode and an electrode provided on the body surface of a patient, said severable tube is heated so as to be melted or dissolved, such that said tube is cut to release said balloon from said catheter.

8. The releasable balloon catheter of claim 7, wherein said severable tube further comprises a tube having an outside diameter of 100 to 1000 microns, a wall thickness of 10 to 400 microns and a length of 2 to 50 mm.

9. The releasable balloon catheter of claim 7, wherein said catheter body further comprises a silicone resin tube, and said severable tube further comprises a polyvinyl alcohol tube.

10. The releasable balloon catheter of claim 7, further comprising a cylindrical cover covering said severable tube so that said tube is prevented from flexural breaking upon catheterization.

11. The releasable balloon catheter of claim 7, further comprising a rigid core material in the inner cavity of said balloon catheter so that the severable tube is prevented from flexural breaking upon catheterization.

12. The releasable balloon catheter of claim 7, further comprising an X-ray impervious metal piece secured to the end portion of said catheter body and to said balloon so as to ascertain the releasing of the balloon from the catheter body by X-ray fluoroscopy.

* * * * *